United States Patent
Wang

(10) Patent No.: US 10,602,989 B2
(45) Date of Patent: Mar. 31, 2020

(54) CAPACITIVE SENSING AND ENCODING FOR IMAGING PROBES

(71) Applicant: Canon U.S.A. Inc., Melville, NY (US)

(72) Inventor: Zhuo Wang, Middleton, MA (US)

(73) Assignee: Canon U.S.A., Inc., Melville, NY (US)

( * ) Notice: Subject to any disclaimer, the term of this patent is extended or adjusted under 35 U.S.C. 154(b) by 602 days.

(21) Appl. No.: 15/255,723

(22) Filed: Sep. 2, 2016

(65) Prior Publication Data

US 2018/0064396 A1    Mar. 8, 2018

(51) Int. Cl.
| | |
|---|---|
| *A61B 18/14* | (2006.01) |
| *A61B 5/00* | (2006.01) |
| *G01D 5/241* | (2006.01) |
| *A61B 8/12* | (2006.01) |
| *A61B 1/00* | (2006.01) |
| *A61B 18/12* | (2006.01) |

(52) U.S. Cl.
CPC .......... *A61B 5/721* (2013.01); *A61B 1/00009* (2013.01); *A61B 1/00172* (2013.01); *A61B 5/0066* (2013.01); *A61B 5/0071* (2013.01); *A61B 5/0084* (2013.01); *A61B 8/12* (2013.01); *G01D 5/2415* (2013.01); *A61B 2562/0233* (2013.01)

(58) Field of Classification Search
CPC .......... A61B 18/14; A61B 1/00; A61B 1/005; A61B 1/045; A61B 18/12; A61B 1/018; A61B 18/1492; A61B 1/0051; A61B 1/00029; A61B 1/00009
See application file for complete search history.

(56) References Cited

U.S. PATENT DOCUMENTS

| | | |
|---|---|---|
| 5,186,177 A | 2/1993 | O'Donnell et al. |
| 5,445,155 A | 8/1995 | Sieben |
| 6,450,964 B1 * | 9/2002 | Webler ..................... A61B 8/12 600/467 |

(Continued)

FOREIGN PATENT DOCUMENTS

| | | |
|---|---|---|
| CN | 102425987 A | 4/2012 |
| EP | 2070468 A1 | 6/2009 |

(Continued)

OTHER PUBLICATIONS

Sun, C. et al., "In vivo feasibility of endovascular Doppler optical coherence tomography", Biomedical Optics Express, Oct. 1, 2012, pp. 2600-2610, vol. 3, No.

(Continued)

*Primary Examiner* — Carl H. Layno
*Assistant Examiner* — Jon Eric C Morales
(74) *Attorney, Agent, or Firm* — Canon U.S.A., Inc., IP Division

(57) ABSTRACT

A probe, system, and method of capacitive sensing for detection of relative rotation of one tube with respect to a fixed tube of a probe is provided herewith. The probe includes an inner core, a concentric cylindrical tube, and at least one inner electrode fixed to the inner core and at least one outer electrode fixed to the cylindrical tube. The electrodes are rotationally aligned and form a capacitive sensor that can sense the rotation angle of the inner core compared to the cylindrical tube. This ability to sense relative rotation angle can be used to detect and/or correct for non-uniform rotational distortion.

19 Claims, 9 Drawing Sheets

(56) References Cited

U.S. PATENT DOCUMENTS

| | | |
|---|---|---|
| 7,366,376 B2 | 4/2008 | Shishkov et al. |
| 7,450,244 B2 | 11/2008 | Xie |
| 7,637,870 B2 | 12/2009 | Flaherty et al. |
| 7,798,011 B2 | 9/2010 | Warren et al. |
| 7,843,572 B2 | 11/2010 | Tearney et al. |
| 7,958,789 B2 | 6/2011 | Hayakawa et al. |
| 8,914,098 B2 | 12/2014 | Brennan et al. |
| 8,920,416 B2 | 12/2014 | Pham et al. |
| 8,928,889 B2 | 1/2015 | Tearney et al. |
| 8,941,392 B1 | 1/2015 | Reese |
| 9,078,570 B2 | 7/2015 | Parks et al. |
| 9,087,368 B2 | 7/2015 | Tearney et al. |
| 9,332,942 B2 | 5/2016 | Jaffer et al. |
| 9,557,154 B2 | 1/2017 | Tearney et al. |
| 2010/0092389 A1 | 4/2010 | Jaffer et al. |
| 2011/0182457 A1 | 7/2011 | Tung et al. |
| 2011/0292400 A1 | 12/2011 | Fleming et al. |
| 2012/0272518 A1 | 11/2012 | Cui et al. |
| 2014/0018669 A1 | 1/2014 | Xu |
| 2014/0323877 A1 | 10/2014 | Courtney et al. |
| 2016/0242845 A1* | 8/2016 | Matsui .................. A61B 1/018 |
| 2017/0135584 A1 | 5/2017 | Tearney et al. |
| 2017/0209049 A1 | 7/2017 | Wang et al. |
| 2017/0360398 A1 | 12/2017 | Hamm |

FOREIGN PATENT DOCUMENTS

| | | |
|---|---|---|
| JP | 2006212356 A | 8/2006 |
| WO | 2014139002 A1 | 9/2014 |
| WO | 2015/116939 A1 | 8/2015 |
| WO | 2015/116951 A2 | 8/2015 |
| WO | 2017/024145 A1 | 2/2017 |
| WO | 2017/024234 A1 | 2/2017 |

OTHER PUBLICATIONS

Mills D.M., et al, "Medical imaging with capacitive micromachined ultrasound transducer (cMUT) arrays", IEEE, Aug. 2004, pp. 384-390, vol. 1; abstract only.

Wygant, I. O., et al, "Integrated Ultrasound Imaging Systems Based on Capacitive Micromachined Ultrasonic Transducer Arrays", IEEE, 2005, pp. 704-707.

Breitenstein, O., "A capacitance meter of high absolute sensitivity suitable for scanning DLTS application", Physical status solidi (a), May 16, 1982, pp. 159-167, vol. 71, No. 1.

High res cap meter with PIC 16F628 by RomanBlack; http://www.romanblack.com/onesec/CapMeter.htm.

* cited by examiner

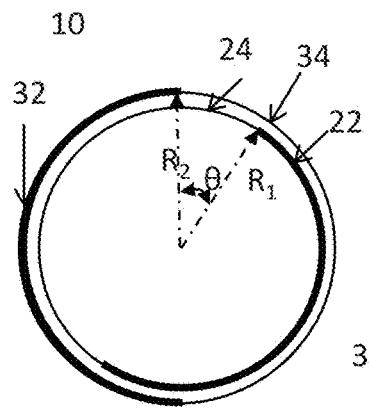
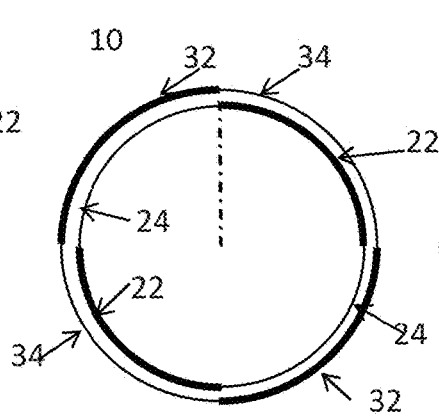
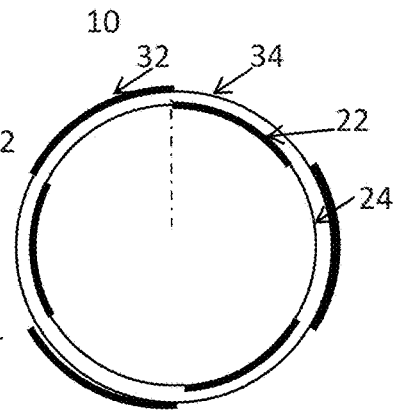
Fig. 1(A)  Fig. 1(C)  Fig. 1(E)
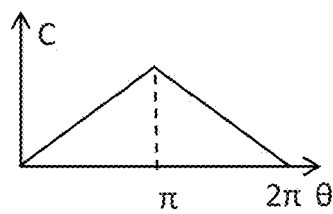
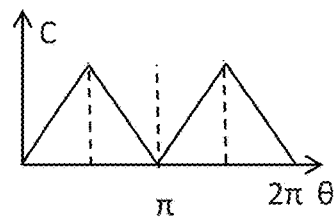
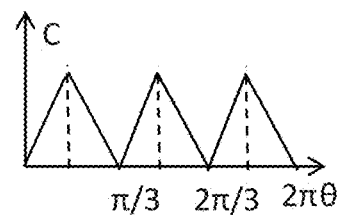
Fig. 1(B)  Fig. 1(D)  Fig. 1(F)
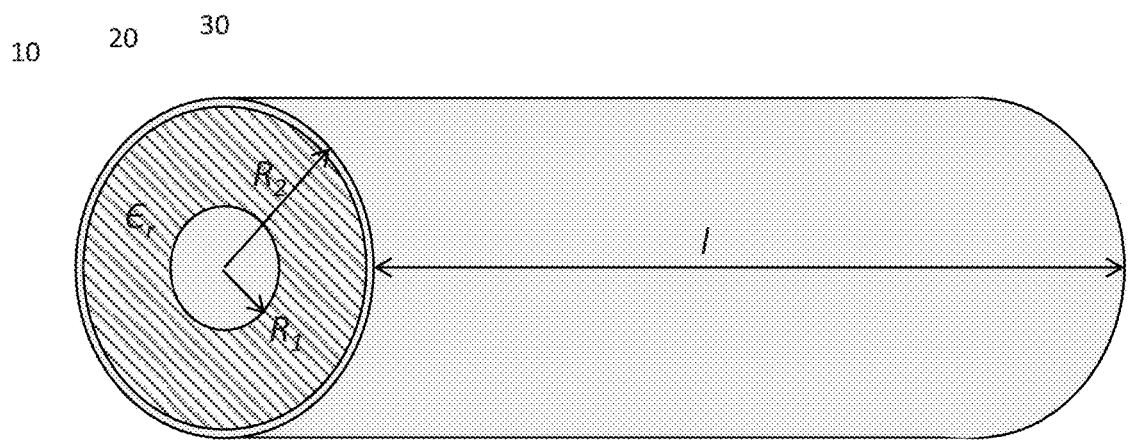
Fig. 2

CAPACITIVE SENSING AND ENCODING FOR IMAGING PROBES

FIELD OF THE DISCLOSURE

The present disclosure relates to capacitive sensing. More particularly, the disclosure exemplifies capacitive sensing used to detect relative rotation of one tube with respect to a fixed tube of a probe

BACKGROUND INFORMATION

Imaging of internal organs is commonly done using a fiber optic catheter. This catheter often includes a pull-back mechanism for viewing a longitudinal section of the internal organ and is often needed to rotate in order to obtain a cross-sectional image and thus provide a three dimensional image of a volume of the internal organ. For applications such as cardiology, interventional radiology and gastroenterology, the imaging system will include optical coherence tomography (OCT) or optical frequency domain imaging (OFDI). Alternatively, it is also possible to obtain images via spectrally encoded endoscopy (SEE), where the linear spatial information is encoded into a spectral line (dispersed line) and the image is formed by rotating the fiber optic probe along its axis.

For these probes, an image is acquired when an inner core is rotated with respect to a cylindrical tube (i.e., the protective sheath of a catheter). However, in these probes, the true angular velocity of the imaging probe is not known, which leads to an artifact referred to non-uniform rotational distortion (NURD). NURD occurs at the point where the imaging signal is directed towards the tissue and can lead to significant distortion of the image and a concomitant reduction in the geometric accuracy of the image.

Optical encoders have been integrated with an OCT probe in order to determine the rotational angle or velocity at the distal end of the probe. This rotational information is further used to detect and compensate for NURD, which can be done via an optical encoder, see, for example, U.S. Pat. No. 8,712,506 for the use of optical encoder to detect the position and the rotation speed. However, in order to process the signals, electrical signals are used to generate the optical sensing signals, and then detect the optical signals using a detector. The detected optical signals are thus translated back into electrical signals for further processing, which introduces additional noise and the devices used for this process add further cost to the system. It is also difficult to miniaturize such systems, which is important for many applications where size is important, such as minimally invasive surgery, needle biopsy, etc.

Thus, there is a need for a sensing mechanism that can produce electrical signals directly for post-processing. It is also desirable to have a sensing mechanism that can produce and detect electrical sensing signals as sophisticated but inexpensive electronics. As the energy in such a process is not transferred from one domain (e.g. optical domain) to a different domain (e.g. electrical domain), no additional actuators and sensors are needed, which poses to lower the total cost of the system as well as minimizing the dimension of the system.

SUMMARY OF EXEMPLARY EMBODIMENTS

According to at least one embodiment of the invention, there is provided an probe comprising: an inner core having a rotational axis, a cylindrical tube arranged concentrically around the inner core, at least one inner electrode fixed to the inner core and aligned parallel to the rotational axis, and at least one outer electrode fixed to the cylindrical tube and aligned parallel to the rotational axis, wherein the at least one inner electrode and the at least one outer electrode together form a capacitive sensor, wherein all electrodes forming the capacitive sensor are rotationally aligned with each other and configured or adapted to sense the rotation angle of the inner core compared to the cylindrical tube.

In some embodiments, a plurality of electrodes are located on the inner core and/or cylindrical tube. For example, both the inner core and cylindrical tube may have 2, 3, 4, 5, 6, or more electrodes; or they may have a different number of electrodes (e.g., the inner core has 2 and the cylindrical tube has 3, or the inner core as 5 and the cylindrical tube has 4.) The electrodes on the inner core and the cylindrical tube may have overlap, they may be symmetrically or asymmetrically shaped and/or positioned. The plurality of electrodes may be located at the distal end of the probe or near the distal end of the probe. For example, they are located within 8, 5, 3, 2, 1 cm or less from the distal end. They may all align along the probe axis or there may be some offset. In some embodiments, the capacitance of the electrodes is between 0.01 pF to 100 nF.

According to other embodiments, there is provided a system including the probe as described above. The system may include illumination and detection optics for, for example, an OCT catheter or an SEE endoscope. The system also includes an electronic detector and an optical detector used during imaging. An analyzer is provided for analyzing the capacitance data and using the date to, for example, correct the images to compensate for NURD or to indicate that NURD is minimal.

In yet other embodiments, there is provided a method of measuring angular rotation in a probe by using capacitance measurements. Image data can then be correlated with the probes rotational position.

These and other objects, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further objects, features and advantages of the present disclosure will become apparent from the following detailed description when taken in conjunction with the accompanying figures showing illustrative embodiments of the present disclosure.

FIGS. 1(A), 1(C) and 1(E) are cross-sectional view of embodiments of medical imaging probes with rotary encoders based on capacitive sensing. FIGS. 1(B), 1(D) and 1(F) are charts showing the relative capacitance for the cross-sectional portions of FIGS. 1(A), 1(C) and 1(E), respectively.

FIG. 2 is a perspective view of a cylindrical probe with an inner core and cylindrical tube.

FIG. 5(E) further includes bumps to prevent the tubes from touching.

FIGS. 16(A) and 16(B) are illustrations of an image before (FIG. 16(C)) and after (FIG. 16(D) interpolation based on the line based method of FIG. 15.

Figure 3A:
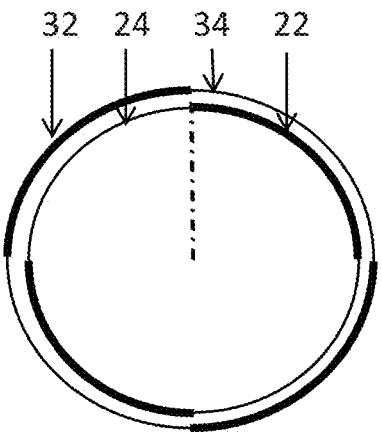
FIGS. 3(A) and 3(C) are cross-sectional views of embodiments of medical imaging probe with rotary encoder based on capacitive sensing and having compensation of the off-center movement (jittering).

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative exemplary embodiments. It is intended that changes and modifications can be made to the described exemplary embodiments without departing from the true scope and spirit of the subject disclosure as defined by the appended claims.

DETAILED DESCRIPTION OF EXEMPLARY EMBODIMENTS

Thus, the present invention provides the use of capacitive sensing for determining angular velocity in a small diameter rotating tube.

Capacitive sensing has been shown to be useful for measuring rotation angles and are used in devices such as capacitive gyroscopes. When there is a need for small gyroscopes, MEMS (micro-electro-mechanical system) technology can produce small capacitive gyroscopes that can integrate the electronics and sensors at the chip level (Steven Nasiri, "A critical review of MEMS gyroscopes technology and commercialization status", InvenSense). The device size can be sub-millimeter and can integrate electronics with sensors on one packaged chip.

There are gyroscopes based on capacitive sensing, such as those depicted in U.S. Pat. Pubs. 2013/0093439 and 2012/0272518 and in CN102425987. However, these devices are not particularly useful when the rotational angle of a device having a small diameter must be measured. Similarly, digital calipers can use the capacitive sensing mechanism. In these devices, the electrodes are integrated with the sensors on one printed circuit board without MEMS technology to provide a high resolution and accurate device with multi-plate capacitive sensors.

The embodiments as described herein can provide relative rotational information between two tubes with different diameters using capacitive sensing. This can, for example, allow for correction for probes such as medical imaging probes. Instead of linear electrodes, the electrodes in the embodiments as described herein are wrapped into an arc, circle, or similar around the rotational axis (i.e., the electrodes are parallel to the rotational axis) and sensing of the capacitance provides rotational sensing. This parallel design allows for the determination of relative rotational angles between two cylinders with different diameters.

In OCT or SEE probes, an image is acquired by rotating an inner core (exemplified as the OCT fiber) with respect to the cylindrical tube (an outer tube which forms a protective sheath for protection).

However, the true angular velocity of the imaging probe is generally not known using conventional techniques. Without knowing the true angular velocity, the artifact referred to non-uniform rotational distortion (NURD) occurs. NURD can lead to significant distortion of the image and a concomitant reduction in the geometric accuracy of the image.

Capacitive sensing can be used to determine relative position. There is also the particular advantage that, since the electrical field can penetrate any dielectric materials of which the probes are generally made, capacitive sensing can be a simple addition to the OCT probe. Both the parallel design and perpendicular design can be implemented for capacitive sensing.

The parallel design shown in the embodiments of FIGS. 1(A), 1(C) and 1E, where the electrodes 22 and 32 are shown. Thus, in FIG. 1(A), the probe 10 includes both an inner core 20 and an cylindrical tube 30, where the cylindrical tube has a portion with a conductive coating 22 and a portion without a conductive coating 24. The inner core has a portion with a conductive coating 32 and a portion without a conductive coating 34. The portions with conductive coatings are electronically conductive and form electrodes 22 and 32. FIG. 1(B) provides the capacitance of the probe of FIG. 1(A) as the inner core is rotated with respect to the cylindrical tube for a full rotation, where the capacitance increases based on the relative position of the electrodes 22 and 32.

FIG. 1(C) shows another embodiment where the probe 10 includes an cylindrical tube 30 having a two portions with a conductive coating 32, and two portions without a conductive coating 34. The inner core similarly has two portions with a conductive coating 22 and two portions without a conductive coating 32. The portions with conductive coatings are electronically conductive and thus four electrodes are formed. FIG. 1D provides the capacitance of the probe of FIG. 1(C) as the inner core is rotated with respect to the cylindrical tube for a full rotation. In this embodiment, the coated and uncoated portions of the embodied probe of FIG. 1(C) are symmetrically placed around the probe.

Similarly, FIG. 1(E) shows another embodiment where the probe 10 includes an cylindrical tube having a three portions with a conductive coating 32 and three portions without a conductive coating 34. The inner core similarly has three portions with a conductive coating 22 and three portions without a conductive coating 24. The portions with conductive coatings are electronically conductive and thus six electrodes are formed. FIG. 1(F) provides the capacitance of the probe of FIG. 1(E) as the inner core is rotated with respect to the cylindrical tube for a full rotation.

In yet other embodiments, each of the inner core and cylindrical tubes may have 5, 6, 7, 8, 9, 10 or more portions having a conductive coating. There may be the same number of portions (of either or both conductive or without a conductive coating) on the inner core and the cylindrical tubes or there may be a different number. For example, the inner core may have a single conductive portion 22 where the majority of the inner core is without a conductive coating 24 and the cylindrical tube may have 4 conductive portions 32 and four portions without a conductive coating 34. In other embodiments, the inner core may have more portions with a conductive coating than the cylindrical tube. The coating can be outside of the tube if the coating material is biocompatible, e.g. gold. If the coating is inside the tube, any conductive materials which are not limited to metals can be used.

FIG. 2 exemplifies a probe 10 having an inner core 20 and an cylindrical tube 30, where portions of either tube may be coated. The inner core 20 has a radius of R1 and the cylindrical tube 30 has a radius of R2. In some embodiments, the cylindrical tube 30 is a catheter sheath with a diameter of, for example, 3 (F), 4 (F), 5 (F), 6 (F) or greater. The inner core may be an imaging endoscope with a diameter of less than 100 μm to a diameter that is slightly smaller than the diameter of the cylindrical tube.

Capacitance Measurements

For the designs shown herein, the capacitance can be defined by:

$$C = \varepsilon_r \varepsilon_0 \frac{A}{d}, \quad (1)$$

where C is the capacitance, in Farads; A is the area of overlap of the two plates, in square meters; $\varepsilon_r$ is the relative static permittivity (sometimes called the dielectric constant) of the material between the plates (for a vacuum, $\varepsilon_r$=1); $\varepsilon_o$ is the electric constant; and d is the separation between the plates, in meters. In the cases shown in FIG. 1, d=$R_2$−$R_1$ where R1 and R2 are the radii of inner core and cylindrical tubes respectively; A=θRl where R=($R_1$+$R_2$)/2, and l is the length of the conductor.

Eq. 1 assumes the diameter of the inner core is very close to the diameter of the cylindrical tube. If the diameters are very different as shown in FIG. 2, the capacitance can be written as $$C = \frac{\varepsilon_r \varepsilon_0 l \theta}{\ln(R_2/R_1)}, \quad (2)$$

where l is the length of the tube. If the condition of ($R_2$−$R_1$)/$R_1$<<1, Eq. 2 will degenerate back to Eq. 1 following the relationship such that ln(1+($R_2$−$R_1$)/$R_1$)≈($R_2$−$R_1$)/$R_1$. For our later discussions, we assume this condition is satisfied for simplicity. Eq. 2 can always be called out for more precise calculations.

Both Eq. 1 and Eq. 2 ignore the edge effect (nonuniform electron distribution near the edge of the electrodes). This effect is usually secondary. To properly consider the edge effect, computer aided simulations such as finite element simulations (FEM) are instrumental to obtain more accurate solutions and can be used in the measurements for the embodiments described herein.

Based on Eq. 1, we can calculate the capacitance for several different scenarios. If the diameter of the tube is 1 mm, distance between the plates is 100 μm, water immersed ($\varepsilon_r$=80), and the total length l is 10 mm, the capacitance is 0.23 nF; if in air, the capacitance is 2.9 pF. These capacitance values, as shown later, can be easily detected with a low cost detection mechanism. If necessary, other types of buffer solutions can be present to modify both the capacitance and the friction between the inner core and the cylindrical tube.

According to Eq. 1, it is obvious that the change of the capacitance is proportional to the changes from both the overlapping area ΔA and the distance between electrodes Δd.

$$\Delta C = \varepsilon_r \varepsilon_0 \frac{1}{d}\Delta A - \varepsilon_r \varepsilon_0 \frac{A}{d^2}\Delta d. \quad (3)$$

Electrode Design

Figure 3C:
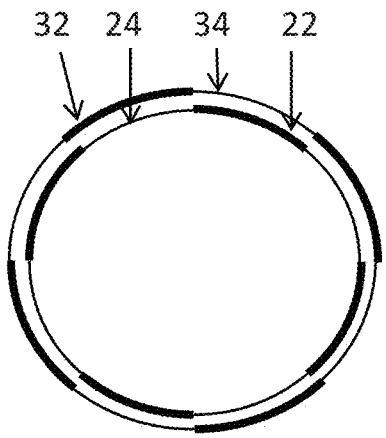
Figure 3B:
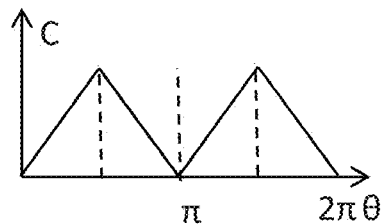
FIGS. 3(B) and 3(D) are charts showing the relative capacitance for the cross-sectional portions of FIGS. 3(A) and 3(C), respectively.
Figure 3D:
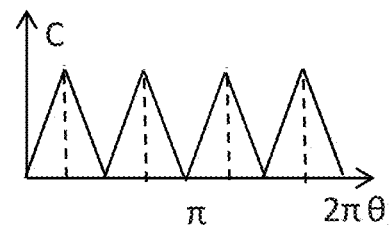

Depending on the electrode design as shown in FIGS. 3(A) and 3(D), it is possible to get varying number of triangular waves during one rotation of the probe. FIG. 3(A) illustrate a probe having two electrodes 32 on the cylindrical tube and two electrodes 22 on the inner core, where the capacitance during the rotation of the inner core is shown in FIG. 3B. FIG. 3(C) illustrates a probe having four electrodes 32 on the cylindrical tube and four electrodes 22 on the inner core, where the capacitance during a full rotation of the inner core is shown in FIG. 3D. Four triangular waves occur with this design. This increased number of triangular waves provides for an increased resolution. However, increasing the number of electrodes means worsening the edge effect. Unwrapping algorithms may also be used to solve the phase ambiguities similar to the digital caliper case.

Asymmetrical electrode design can be used to indicate clockwise and counterclockwise rotation, similar to the probe design of FIG. 1.

According to Eq. 3, the off center movement of the electrodes, i.e. jittering, will also affect the capacitance. This can provide an undesirable effect as it will introduce errors. Thus, it is preferred to design the location of electrodes to avoid off-center movements and the creation of such errors. A design having four electrodes (e.g., the design of FIG. 1C) may be of particular interest in some applications since this design can automatically cancel out the unwanted signal from jittering of the tube and it can provide detection the lateral translation in both X and Y direction, as well as lateral rotation and longitudinal translation.

FIGS. 3A-3D shows design examples that are capable of compensating the jittering. When the inner core is moving toward the cylindrical tube, as illustrated by FIG. 3(A), the distance Δd for half of the electrodes are positive and for another half of the electrodes are negative. As a result, at least on the first order this jittering effect is canceled out.

Figure 4A:
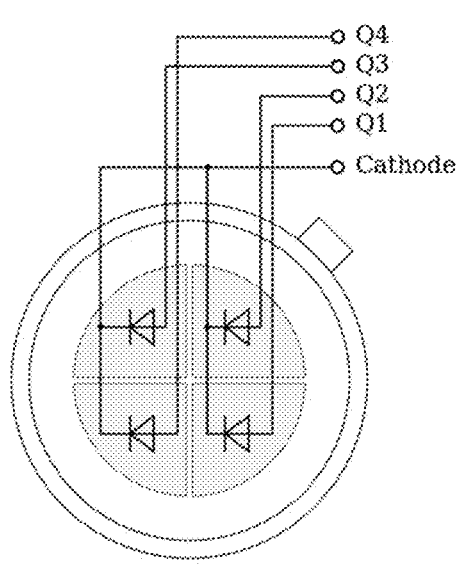
FIG. 4(A) is diagram of an exemplary quadrant photodetector.
Figure 4B:
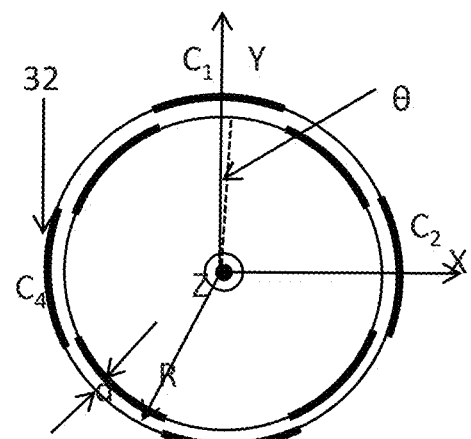
FIG. 4(B) is a cross-sectional view of an embodiment of a medical imaging probe with rotary encoder based on capacitive sensing and FIG. 4(C) shows the relative capacitance for the cross-sectional portion of FIG. 4(B).
Figure 4C:
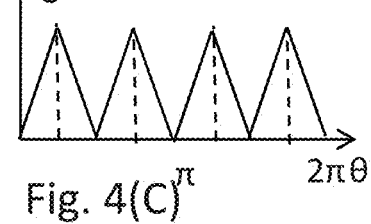

In some embodiments, other parameters, such as such as $\Delta x$, $\Delta y$, $\Delta z$, and $\Delta\theta$ are detected as well. This can be done using a quadrant detection. FIGS. 4(A)-4(C) show a comparison between the typical quadrant photodetector and the proposed capacitive quadrant detection. Similar equations used for quadrant photodetection can be applied here as well. FIG. 4(A) shows the schematic of a widely used quadrant photodetector. As a comparison, if four electrodes are present, as shown in FIG. 4(B), it is possible to detect not only the rotation angle. A Cartesian coordinate system is assumed here as shown in FIG. 4(B) where the Z axis is extending along the probe axis. FIG. 4(C) shows the quadrant capacitance detection where four electrodes are used. A Quadrant photodetector such as the one shown in FIG. 4(A) may be sued to detect the capacitance of FIG. 4(C). Similarly, more than four electrodes may also be used with the same or other detectors.

Similar equations used for quadrant photodetection can be applied here. Equations 4-6 show some relationships to detect the probe translation $\Delta x$, $\Delta y$ and probe rotation $\Delta\theta$.

$$\Delta C_2 - \Delta C_4 = 2\varepsilon_r\varepsilon_0 \frac{A}{d^2}\Delta x, \quad (4)$$

$$\Delta C_1 - \Delta C_3 = 2\varepsilon_r\varepsilon_0 \frac{A}{d^2}\Delta y, \quad (5)$$

$$\Delta C_1 + \Delta C_2 + \Delta C_3 + \Delta C_4 = 4\varepsilon_r\varepsilon_0 \frac{1}{d}R\Delta\theta, \quad (6)$$

where R is defined as the arithmetic average of the radii of the inner core and the cylindrical tube.

Figure 5A:
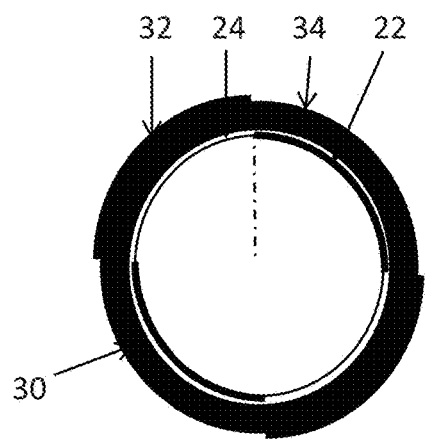
FIGS. 5(A), 5(C) and 5(E) are cross-sectional view of embodiments of medical imaging probes with rotary encoders based on capacitive sensing where conductive material can be either inside, in the middle, or outside the inner core or cylindrical tubes.

As explained before, the conductive coating can be outside of the external tube if it is biocompatible (e.g. gold). This configuration is shown in the left plot of FIG. 5(A) where conductive coating 32 is external to the thick cylindrical tube 30.

Figure 5C:
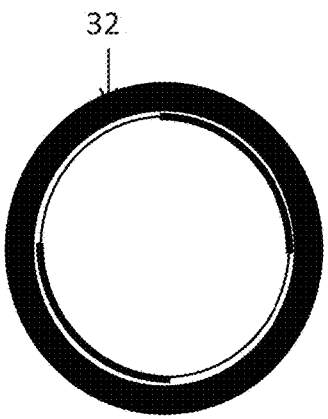

It is also possible to have laminated tubing with conductive layer built inside the material as shown in FIG. 5(C) where the conductive coating 32 is laminate within the cylindrical tube 30 and the inner core has conductive 22 and non-conductive 24 portions. One catastrophic failure mode for the capacitive sensing is the touching of the electrodes. For both cases here this failure mode is naturally avoided. Similarly as long as the conductive coating on the inner core is not on the outside, this failure node is also avoided. If the conductive coating is inside for the cylindrical tube and is outside for the inner core, it is possible that the electrodes will touch each other.

Figure 5E:
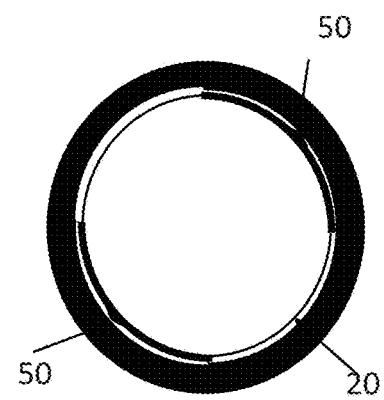
Figure 5B:
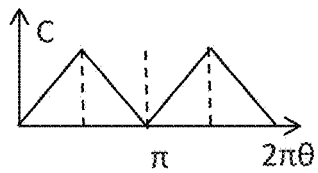
FIGS. 5(B), 5(D) and 5(F) are charts showing the relative capacitance for the cross-sectional portions of FIGS. 5(A), 5(C) and 5(E), respectively.
Figure 5D:
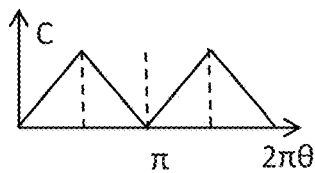
Figure 5F:
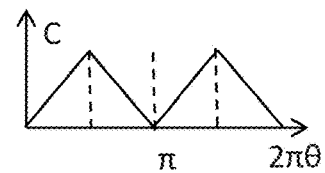

In order to avoid contact when the electrodes are not separate by a tube or laminate, non-conductive bumps 50 can be added to the outside of the inner core 20 to prevent the electrodes from touching, which is shown in FIG. 5E. In this instance, the bumps 50 are located on the conductive portion 22. However, in other configurations the bumps 50 may be located on the non-conductive portion 24 or on the cylindrical tube 30. For each of these embodiments, the capacitance of the apparatus is shown for one full rotation (FIGS. 5(B), 5(D), and 5F.)

In some embodiments, the inner core (or cylindrical tube) can be coated in longer length so that the system will work when two tubes are not well aligned longitudinally or there is an offset between the tubes. For an extreme case, it is possible to extend the electrode throughout the whole length of the inner core or cylindrical tube.

Figure 6:
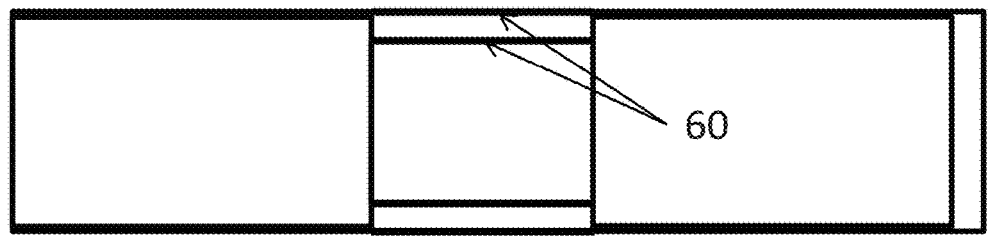
FIG. 6 is a diagram showing an embodiment having stepwise tubing to avoid the contact of the electrodes.

Besides the embedded tubing (laminated tubing) design of FIG. 5(C) and the stop bump design of FIG. 5E, it is also possible to have a stepwise tubing design as shown in FIG. 6 in order to avoid the contact of the electrodes 60. Again, it is possible to have either inner electrodes or outer electrodes significantly longer so that the system will work when two tubes are not well aligned or there is an offset between the tubes. For an extreme case, it is possible to extend the electrode throughout the whole inner tube or outer tube.

Figure 7A:
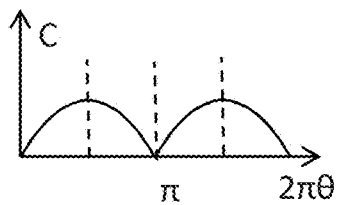
FIGS. 7(A), 7(B) and 7(C) are cross-sectional view of embodiments of medical imaging probes with rotary encoders based on capacitive sensing showing overlapping electrodes (FIG. 7A), unsymmetrical electrodes (FIG. 7B) and electrodes that are both unsymmetrical and uneven (FIG. 7C).
Figure 7B:
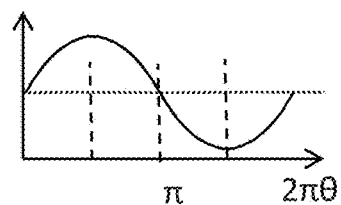

Sensor configurations with different electrode configurations are also contemplated. FIG. 7 illustrates an embodiment where the electrodes are overlapping (FIG. 7A), where the electrodes are unsymmetrical (FIG. 7B), and where the sensor has an unequal number of electrodes on the cylindrical tube compared to the inner core (FIG. 7C).

Figure 7C:
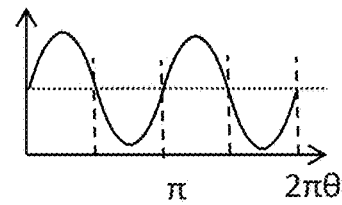
Figure 8A:
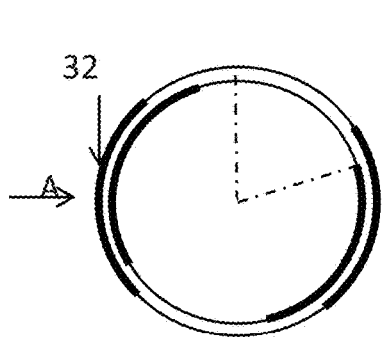
FIG. 8(A) is a cross-sectional view of an embodiments of a medical imaging probe with rotary encoders based on capacitive sensing.
Figure 8B:
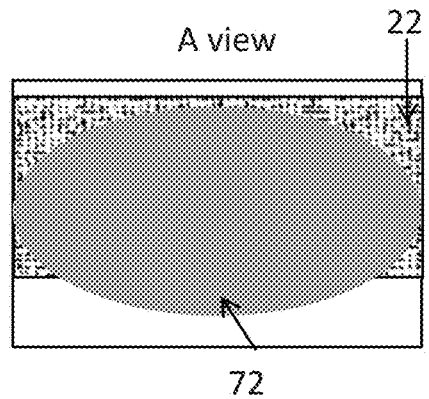
FIG. 8(B) is a flattened view through point "A" of the embodiment of FIG. 8(A).
Figure 9A:
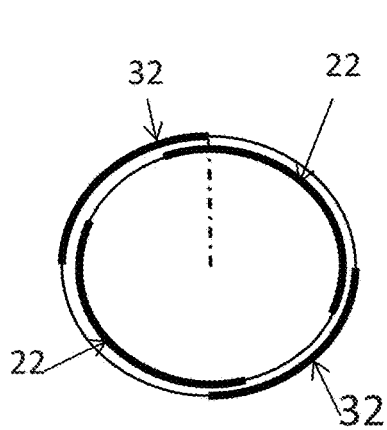
FIGS. 9(A), 9(B), and 9(C) are cross-sectional views of embodiments of a medical imaging probe with rotary encoders based on capacitive sensing, where FIG. 9(A) has a total of 43 electrodes, FIG. 9(B) has a total of 2 electrodes, and FIG. 9(C) has a total of 9 electrodes.
Figure 9B:
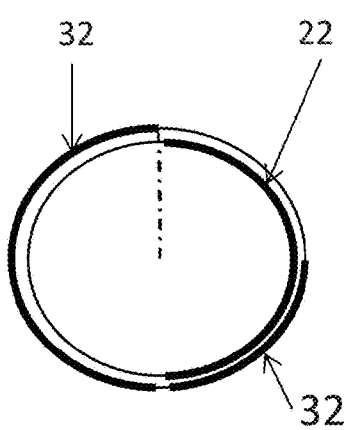
Figure 9C:
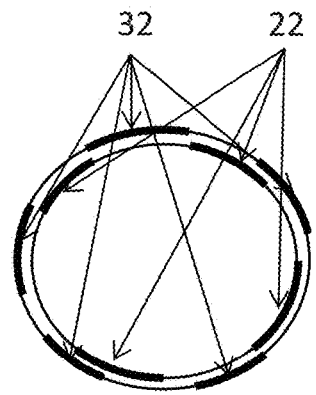

In order to improve the sensitivity, it is possible to design the shape of the electrodes in order to form a sinusoidal waveform as shown in FIG. 7(A)-7C. Depending on the pad design, the output signal can shift from triangular wave to sinusoidal wave or other waveforms. Phase shifting and other sensitive phase detection methods can improve the sensitivity. An example of a different pad design is shown in FIGS. 8(A), 8(B), and FIGS. 9(A)-9C. In FIGS. 8(A) and 8(B), the electrode on the inner core 22 is rectangular but the electrode on the cylindrical tube 72 is elliptical. In FIG. 9(A), the probe 10 includes both an inner core 20 and an cylindrical tube 30, where the cylindrical tube has two portions with a conductive coating 22 and two portion without a conductive coating 24. The inner core has two portions with a conductive coating 32 and two portions without a conductive coating 34. The portions with conductive coatings are electronically conductive and form electrodes 22 and 32. Similarly, FIG. 9(B) has only a single electrode 22 formed on the inner core and a single electrode 32 formed on the cylindrical tube. FIG. 9(C) has four electrodes 22 formed on the inner core and five electrodes formed on cylindrical tube.

In other embodiments, the pad design can be similar to the one described in U.S. Pat. Pub. 2013/0093439, herein incorporated by reference for this feature. If one full modulation is present, one can take full advantage of the mature phase shifting and other sensitive phase detection methods for improved sensitivity and accuracy.

In some embodiments, the electrodes are connected to one common wire to minimize the wire capacitance. In some embodiments, these wires can be moved away from the electrodes to minimize the capacitance values as well. The wires can be specifically designed to filter the residue capacitance, e.g. double (or higher) the frequency of the wire overlaps by dividing wires or lower the frequency of the wire overlaps by combining wires.

Figure 10A:
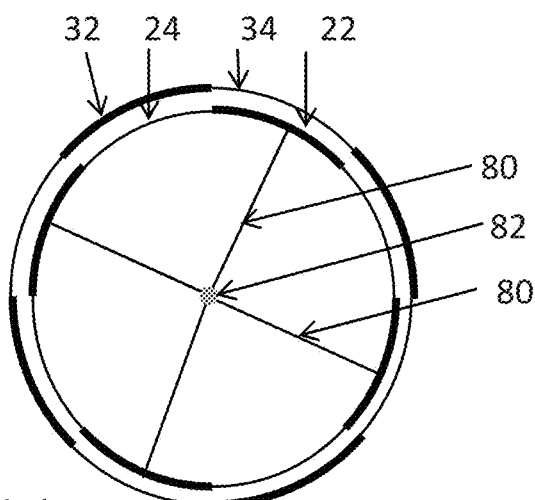
FIG. 10(A) is a cross-sectional view of an embodiment of a medical imaging probe with rotary encoders based on capacitive sensing. This embodiment shows minimization of the residue capacitance from the long wire.
Figure 10B:
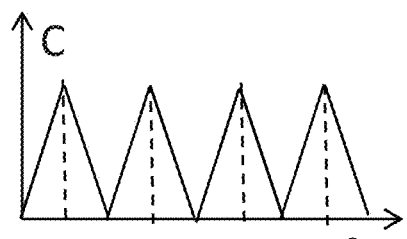
FIG. 10(B) is a chart showing the relative capacitance of FIG. 10A.

In some embodiments, the extra residue capacitance introduced by having long hanging wires will be countered. The need for this feature will depend on the design of the probe. One method is calibration for individual devices. Alternatively, according to Eq. 1, since the capacitance is inverse proportional to the distance d, the wires 80 are located away from the electrodes to minimize the capacitance coming from the wires. It is also helpful to combine several wires 80 to one wire 82 as shown in FIG. 10A. This embodiment is particularly useful when there is no need for optical components to be located in the center of the cylindrical tube at the location of the wires. Additional design to filter the "noise" are also contemplated. One example is to double (or higher) the frequency of the wire overlaps by dividing wires.

Another example is to lower the frequency of the wire overlaps by combining wires. Yet another example is to radiate (couple) the signal (RF signal) directly out using antenna. Additional modulation and demodulation may used on this example as well.

Probe Design

Figure 11:
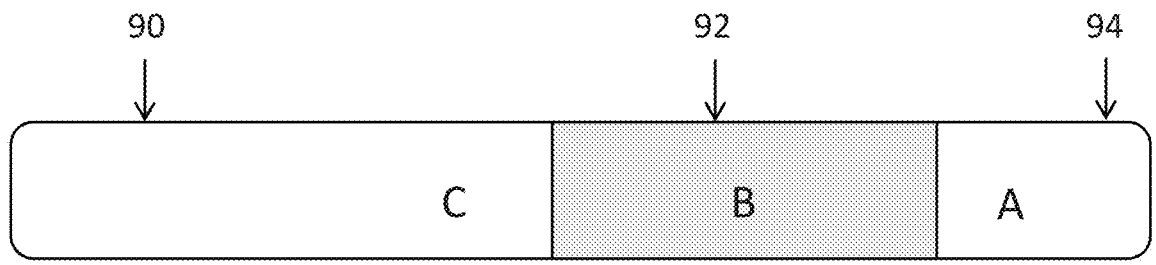
FIG. 11 is an illustration of an embodiment showing potential placement of the capacitive sensing portion on the probe.

The exemplary probe as shown in FIG. 11 provides shows the outer cylindrical tube having a proximal end 90, an imaging window 92 that is transparent, and a distal end 94 of a probe 10. The imaging window 92 is the region through which light from an imaging component (a part of the inner core) is transmitted into the surrounding tissue. The imaging window may be, for example, a cylindrical polymer extrusion suitable for use in the coronary vasculature, where the inner tube containing the imaging component at the distal end rotates and pulls back to create a 3-D image. The imaging window 92 is substantially transparent to imaging light (for example light between 400 and 1000 nm or a region there within).

In some embodiments, the imaging window has a hydrophilic coating on its outer surface. This provides for facile movement of the probe through an in vivo environment. A lubricious material may be provided on the outer surface of the imaging window (e.g., FEP, or PTFE (Teflon®) to allow the imaging core to rotate freely within the imaging window.

The probe as described herein may be a catheter where the cylindrical tube is the catheter sheath. The imaging component is inside the catheter, where the imaging component can image in vivo via OCT, fluorescence, IVUS, spectrally encoded endoscopy, or other imaging methods. The imaging catheter may be adapted for creating a cross-sectional image from an in vivo sample. In some embodiments, the imaging component consists of a connector, drive shaft, optical fiber and distal optics, which are rotated and pulled back inside of the catheter sheath (the cylindrical tube), which stays stationary during imaging. When deployed in a blood vessel, the system can produce a 3-D reconstruction of the blood vessel for, for example, diagnosis of coronary artery disease, or other areas of the body of interest to the clinician such as gastrointestinal (GI), urological (URO), biliary tree, peripheral vasculature, etc.

The electrodes can be located either on the distal end 94 or the proximal end 90 that is proximal to the imaging window 92. In some embodiments, the electrodes can be located on the imaging window 92. While the imaging window must be substantially transparent, thin electrodes will not significantly reduce the image quality obtained from the imaging component. In other embodiments, the electrodes are located on the distal end 90. In other embodiments, the electrodes are located proximal to the imaging window 94, where a portion of each electrode is located within 2 mm, within 4 mm, within 6 mm, within 10 mm, or within 20 mm of the imaging window. To best estimate the NURD, the electrodes should be as close to the imaging window as reasonably possible. In some embodiments, the electrodes encompass more than one region.

NURD is usually distributed along the whole probe. In order to correct the NURD for better imaging results, the NURD detection portion is placed close to the imaging window 92. The location of the capacitive sensing portion (i.e., the electrodes) is thus at either the distal end 94 or the proximal end 90, where the capacitive sensor is preferably located close (e.g., within a few millimeters) to the imaging window 92. The length of the electrodes can, for example, be as small as several millimeters or can extend to several or multiple centimeters.

To create a capacitive sensor and detect NURD, the electrodes are rotationally aligned. Thus, upon rotation of either the inner our cylindrical tube, the electrode(s) on the inner core rotate relative to the electrodes on the cylindrical tube such that an electrode on one tube is in proximity and out of proximity to each of the electrode on the other tube during a rotation of the tube. When the two electrodes are in proximity, there will be measurable capacitance from the electrode(s).

The location of the electrodes on the tube is not critical to the capacitive sensing aspect of the invention and can be modified based on the probe configuration, use, or manufacture considerations. However, at least one electrode is fixed on the inner core and at least one electrode is fixed on the cylindrical tube. As discussed above, the plurality of electrodes can be located at one or more of the following locations: on the inside of the inner core, on the outside of the inner core, on the inside of the cylindrical tube, on the outside of the cylindrical tube, imbedded in the inner to, and/or imbedded in the cylindrical tube. When located or fixed on a tube, the electrode may be laminated or deposited onto the surface of the tube, fixed to the tube via an adhesive or a mechanical fixture such, anodized and patterned, etc.

Depending on the application, sometimes it is desired to have the capacitive sensing portion overlaid with the imaging window so that direct compensation of NURD for optical or other imaging modalities is possible. If this is the case, the majority of the window transparency is maintained.

Either hydrophilic or hydrophobic coatings can optionally be applied on the contacting surfaces to minimize the friction between the tubes. For example, both the outside of the inner core and the inside of the cylindrical tube can have a hydrophilic coating. This can minimize the friction even without the presence of a buffer solution in the probe.

Electrode Formation

The inner core and cylindrical tubes both have at least one electrode fixed on the tube. This can be on the inside or outside of the tube, or it could, in some cases, extend all the way through the tube or alternatively be located within the tube (e.g., as a laminated layer.) For in vivo probes, the coating on the outside of the cylindrical tube must be made from a biocompatible coating material, e.g. gold. If the coating is inside the tube, any conductive materials which are not limited to metals can be used.

The material of the electrodes can be, for example, metals such as gold or optically transparent but electrically conductive materials including but not limited to ITO or PEDOT:PSS. Other electrode materials include the conductive polymers from DuPont (e.g. stretchable inks for wearable electronics, or printed silver or aluminum) and the conductive glass ITO (Indium Tin Oxide).

If the electrodes are collocated with the imaging window, and an optically opaque element (e.g., gold) is used, the thickness of the gold needs to be very thin so as not to substantially detract from the image formed using the imaging window. Thus, a very thin layer of an electrode material may be coated on the window so that it is still substantially optically transparent over the region of interest but has electrical conductivity.

Figure 12:
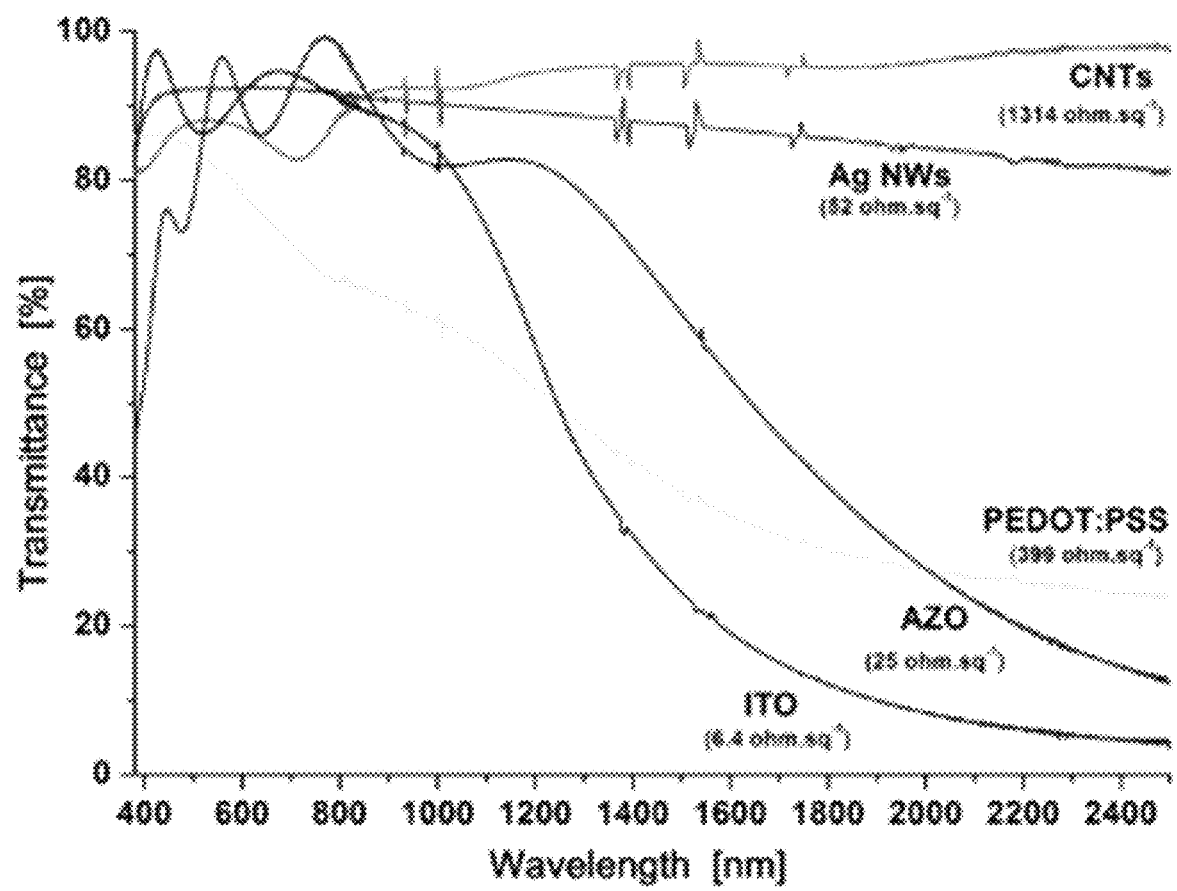
FIG. 12 is a chart showing the transmittance for a range of wavelengths for several conductive materials for use in several embodiments.

In contrast, when an optically transparent but electrically conductive material is used, the electrode portion can be substantially thicker. One example of a transparent material is PEDOT:PSS, which has a good transmissivity in visible light. Another example is the use of thin film ITOs (e.g., 200 nm thick) as the electrodes. Other exemplary conductive materials that may be applied to the window are shown in the graph of FIG. 12. These materials may also be used in instances where the proximal or distal portion of the probe is covered instead of (or in addition to) the window.

When the electrodes are not co-located with the imaging window (i.e., when the electrodes are on the proximal or distal ends), both the optically opaque and optically transparent materials may be formed into either thick or thin electrodes. The thickness will depend upon ease of fabrication and quality as well as the conductive properties of the materials.

The laminate, such as described in FIG. 5(C), may be made by traditional lamination or may be made by a printing method, such as the one described in U.S. Pat. No. 7,958,789 where a dielectric layer and the electrodes are formed by a printing method using a dielectric layer coating containing a formation component of the dielectric layer and/or an electrode coating containing a formation component of the electrode.

System

Figure 13:
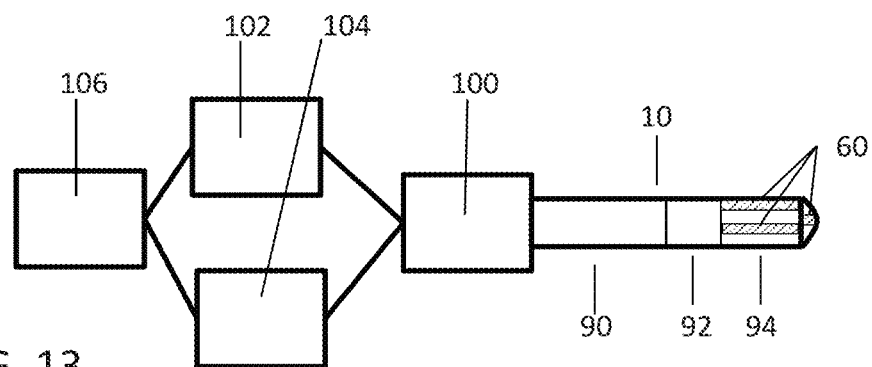
FIG. 13 is a block diagram of an embodiment showing the probe system.

FIG. 13 exemplifies an embodiment that is a system containing a probe 10 having capacitive sensing. The probe 10 has electrodes 60 on both the inner core 20 and cylindrical tube 30, where the electrodes 60 are arranged radially at the distal end 94 of the probe. The probe 10 is connected to a rotary junction 100 that rotates the inner core with respect to the cylindrical tube. The optical signal is sent to an optical detector 102 and the electronic signal is sent to an electronic detector 104, where the electronic detector 104 may be different or the same as the optical detector 102 when the optical detector can measure capacitance. The system includes an imaging console 106 which includes, for example, a computer and a light source. The imaging console 140 can also be connected to the rotary junction 100 which rotates the probe 10. The console 106 is configured to calculate the relative rotational information between two tubes and provide information that can be used to correct the image signal obtained from the optical detector.

This system may be used with a variety of imaging modalities, such as OCT, spectrally encoded imaging, ultrasound, fluorescence and other modalities where, due to the imaging or other reasons, a probe element is rotated. It may be used in any cavity, such as an organ, luman, or body cavity.

This system may be used, for example, with an OCT system. One example of an OCT system is an OCT probe and detector used in coronary vasculature for diagnosis and/or treatment of coronary diseases and conditions. The system may also include other imaging modalities. In use, for example, the probe is inserted into a blood vessel by means of a guidewire. Then, the probe can undergo pullback where the probe tip moves along the imaging window where images of the surrounding tissue are obtained. At the same time, the electrodes 60 are used to sense the capacitance.

Imaging systems that may be used with the probes and methods as described herein include, but are not limited to, the OCT imaging systems disclosed in U.S. Pat. Nos. 7,872,759; 8,289,522; and 8,928,889 to Tearney et al. and arrangements and methods of facilitating photoluminescence imaging, such as those disclosed in U.S. Pat. No. 7,889,348 to Tearney et al., as well as the disclosures in U.S. Patent Publication Nos. 2012/0101374 and 2009/0192358, each of which patents and patent publications are incorporated by reference herein in their entireties.

This system may be used, for example, with an SEE probe and detector(s) for the spectrally encoded light. The system may also include other imaging modalities. SEE imaging systems that may be used with the probes and methods as described herein include Such exemplary SEE systems are described, for example, in U.S. Pat. Nos. 6,341,036; 7,447, 408; 7,551,293; 7,796,270; 7,859,679; 8,045,177; 8,145, 018; 8,838,213; 9,254,089; 9,295,391; and Patent Application Publication Nos. WO2015/116951 and WO2015/116939, each of which patents and patent publications are incorporated by reference herein in their entireties.

In some embodiments, a sub-pF capacitance meter, such as one that senses capacitance as small as 0.01 pF with a range of 0.01 pF to 47000 µF, may be used as the electric detector X. The sub-pF capacitance meter may be configured using a resonance-tuned LC bridge or a meter based on PIC, where PIC stands for Peripheral Interface Controller, and PIC microcontrollers are based on a family of modified Harvard architecture microcontrollers. See, for example, Breitenstein, Physica Status Solidi (a) vol. 71(a) p 159-167, 16 May 1982. Also see, for example, http://www.roman-black.com/onesec/-CapMeter.htm.

In some embodiments, the system as described herein includes advanced feedback loops and/or signal conditioning electronics to minimize noise and other forms of error. In some embodiments, the feedback loops and/or signal conditioning electronics used can be similar to those found in touch screen devices, which are also based on the capacitive sensing mechanism. For example, circuits can be integrated with the sensing pads similar to the caliper and MEMS devices or the like. The touch screen devices are adapted to minimize, for example, false touches and multiple touches. Thus, this technology allows for the sensors as described here to handle different situations advantageously with the use of advanced feedback loops and signal conditioning electronics.

There are many advantages of the capacitive sensing and encoding for imaging probes as described herein. First the capacitive sensor can be seamless incorporation to existing systems, with no need for, for example, photo-sensors as the signal is electrical in nature. For example, the capacitive sensor can be added to the probes described in U.S. Pat. No. 7,872,759 and U.S. Pat. Pub. 2011/0237892, which are both incorporated by reference for this feature.

Second, the capacitive sensor is cost effective as inexpensive microcontrollers can be used for detection. For example, special laminated tubing can be introduced to cut down the cost further. Third, the design has an adjustable fast response time depending on the combined resistance and capacitance (RC). This can be important for real time image correction. Last, the design will generate little heat as it is an RC circuit. Even less heat will be generated if we can build an LC circuit or an RLC circuit. The whole capacitive sensor can also be made biocompatible as well to facilitate its use in patients.

One big advantage for capacitive sensing is that the sensing speed can be very fast, e.g. MHz. This means the speed and the location of the tube can be sensed in real time, which makes possible to compensate the NURD in real time as well. As the sensor's detection mechanism is very compact and inexpensive as well, it is possible to even integrate the sensing electronics with the probe similar to the gyroscope in smart phones.

A system for, for example, SEE or OCT would also include an optical detector such as a PMT, photodiode, or line scan camera.

The system may further comprise an analyzer, which may be part of a CPU, that can modify the image data (e.g., the SEE or OCT image data) based on the information from the detected capacitance. This modification may be provided in substantially real time or may be delayed.

After the capacitive sensors detect NURD, this information can be used to correct an image or a series of images. The correction may be done by, for example, re-mapping each image based on the exact rotational position. The capacitive sensors behave similar to an encoder which records the angle of rotation at a given time at the distal end of the probe. Whenever data are taken by the imaging sensor, it is possible to know from the capacitive sensors the exact angle of the rotation. If no NURD is present, the angle spacing between data points should be equal. If there is NURD, the angle spacing can be obtained by the information provided by the capacitive sensors. For both cases it is preferred to change from the polar coordinates, i.e. the coordinates in which the data are acquired, into Cartesian coordinates. The images in the Cartesian coordinates may need to be further resampled in order for proper display.

Figure 14:
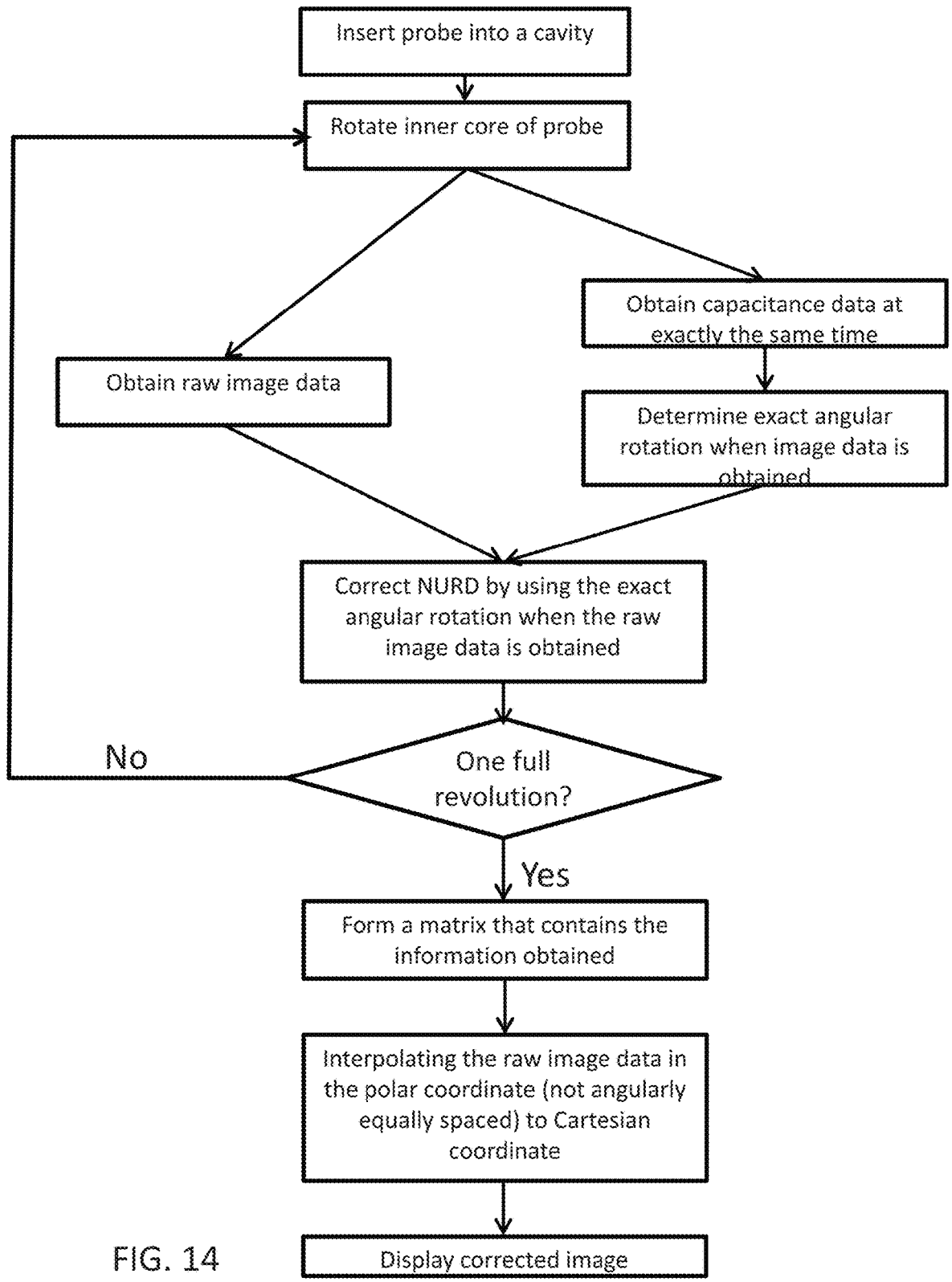
FIG. 14 is a flow chart showing an exemplary frame based method of use for the medical imaging probe.
Figure 16A:
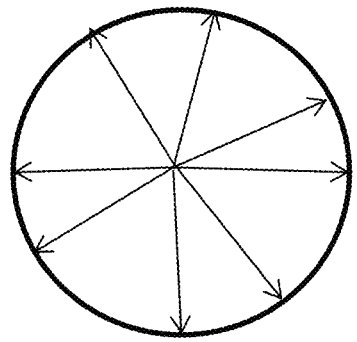
FIGS. 16(A) and 16(B) are illustrations of an image before (FIG. 16(A)) and after (FIG. 16(B) interpolation based on the frame based method of FIG. 14.
Figure 16B:
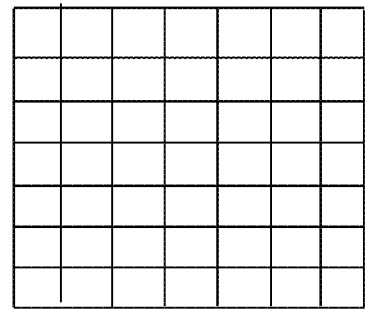

In use, as exemplified in the method shown in FIG. 14, the probe is first inserted into a cavity and rotated in order to form an image (e.g., an OCT or SEE image.) During rotation in this frame-based method, raw image data is obtained at the same time that capacitance data is obtained and the exact angular rotation when the image data is obtained is determined. NURD is corrected by using the exact angular rotation when the raw image is obtained. If this process included one full revolution, a matrix is formed that contains the information obtained. The one full revolution can be decided, for example, based on the motor encoder, a separate sensor, or the capacitance sensor itself. After the matrix is formed, the raw image data is interpolated in the polar coordinate to Cartesian coordinate where, as shown in FIGS. 16(A) and 16(B), the non-equally spaced polar coordinate from before interpolation (FIG. 16(A) becomes an equally spaced Cartesian coordinate (see FIG. 16(B). The corrected image is then displayed.

Figure 15:
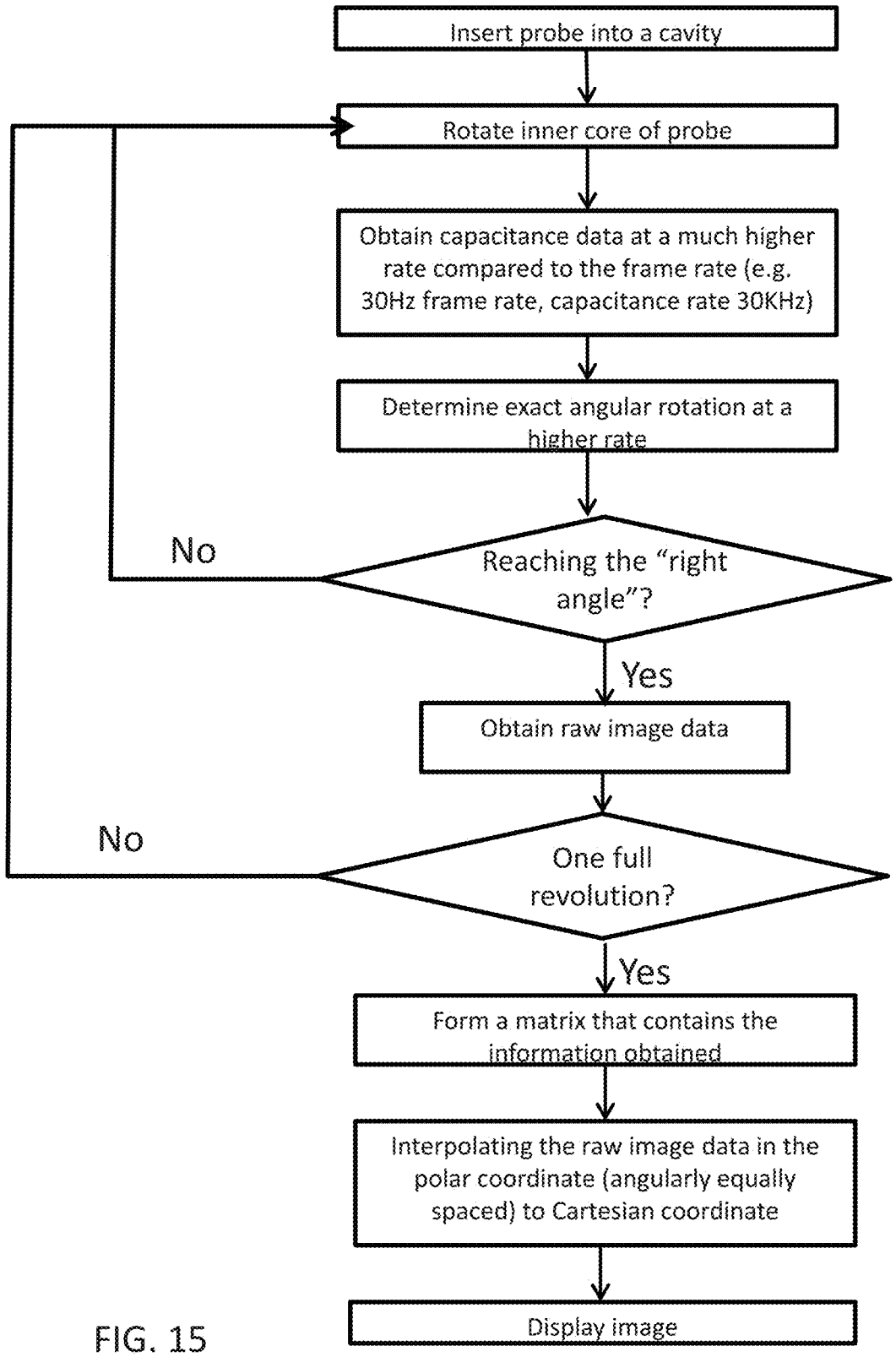
FIG. 15 is a flow chart showing an exemplary line based method of use for the medical imaging probe.
Figure 16C:
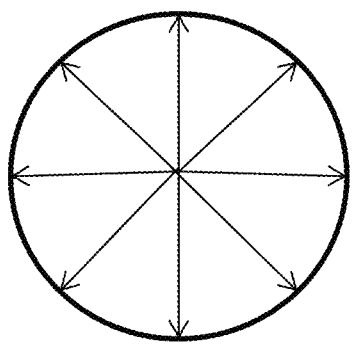
Figure 16D:
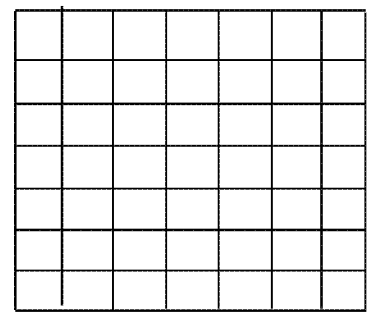

Another exemplary method is shown in FIG. 15, the probe is first inserted into a cavity and rotated in order to form an image (e.g., an OCT or SEE image.) During rotation in this line-based method, the capacitance data is obtained at a much higher rate compared to the frame rate (e.g., 30 Hz frame rate and 30 kHz capacitance rate). In this method, you determine the exact angular rotation at a higher rate. The "right angle," which is determined by the sampling rate within one full revolution is defined. For example, if 1000 lines for 360 degrees, the right angle will be 0.36 degrees, 0.72 degrees, 1.08 degrees. If the right angle is reached, the raw image data is obtained, and if a full revolution is reached, such as described for FIG. 14, a matrix is formed that contains the information obtained. The one full revolution can be decided, for example, based on the motor encoder, a separate sensor, or the capacitance sensor itself. After the matrix is formed, the raw image data (which is angularly equally spaced as shown in FIG. 16(C)) is interpolated in the polar coordinate to Cartesian coordinate (see FIG. 16(D). The corrected image is then displayed.

Embodiment(s) of the present invention can also be realized by one or more computers that reads out and executes computer executable instructions (e.g., one or more programs) recorded on a transitory or non-transitory storage medium to perform the functions of one or more of the above-described embodiment(s) and/or that includes one or more circuits for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). In one embodiment, the imaging console 140 includes a computer unit and one or more display unit is connected to the console 140 via a high definition multimedia interface (HDMI). Optionally, a separate image server is another computer unit connected to the console 140 connected via an Ethernet cable or the wireless access point.

Figure 17:
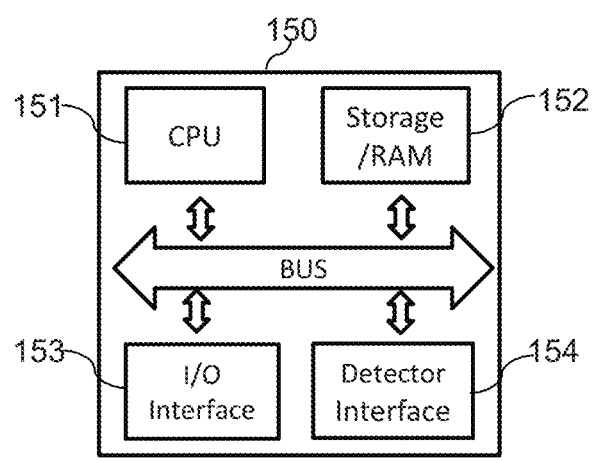
FIG. 17 is a computer unit of an embodiment as described herein.

The computer units can be described by FIG. 17 where a command can be transmitted to the computer system 151 via a user interface unit/arrangement that may be located on the imaging console 140. A touch panel screen can be includes as part of the user interface unit/imaging console, but key board, mouse, joy-stick, ball controller, and foot pedal can also be included. The user can cause a command to be initiated to observe inside the human body through the exemplary front-view SEE probe using the user interface unit/imaging console. For example, when the user inputs a command, the command is transmitted to the central processing unit for execution thereby.

Computer system 150 can include CPU 151, Storage/RAM 152, I/O Interface 153 and Detector Interface 154. Also, Computer system 150 may comprises one or more devices. For example, the one computer may include components 151, 152 and 153 and other computer may include component 154.

The CPU 151 is configured to read and perform computer-executable instructions stored in the Storage/RAM 152. The computer-executable instructions may include those for the performance of the methods and/or calculations described herein. For example, CPU 151 calculates the angular momentum and uses that information to provide a new image. Storage/RAM 152 includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 152 may store computer-readable data and/or computer-executable instructions. The components of the computer system 150 communicate via a bus.

The I/O interface 153 provides communication interfaces to input and output devices, which may include a keyboard, a display, a mouse, a printing device, a touch screen, a light pen, an optical storage device, a scanner, a microphone, a camera, a drive, communication cable and a network (either wired or wireless).

The detector interface 153 also provides communication interfaces to input and output devices. The detector may include, for example a photomultiplier tube (PMT), a photodiode, an avalanche photodiode detector (APD), a charge-coupled device (CCD), multi-pixel photon counters (MPPC), or other. Also, the function of detector may be realized by computer executable instructions (e.g., one or more programs) recorded on a Storage/RAM 152.

Definitions

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means, for example, within 10%, within 5%, or less. In some embodiments, the term "about" may mean within measurement error.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is understood that the present disclosure is not limited to the disclosed exemplary embodiments. The scope of the following claims is to be accorded the broadest interpretation so as to encompass all such modifications and equivalent structures and functions.

What is claimed is:

1. A probe comprising:
   an inner core having a rotational axis,
   an cylindrical tube arranged concentrically around the inner core,
   at least one inner electrode fixed to the inner core and aligned parallel to the rotational axis, and
   at least one outer electrode fixed to the cylindrical tube and aligned parallel to the rotational axis,
   wherein the at least one inner electrode and the at least one outer electrode together form a capacitive sensor, wherein all electrodes forming the capacitive sensor are rotationally aligned with each other and configured or adapted to sense the rotation angle of the inner core compared to the cylindrical tube.

2. The probe of claim 1, wherein at least two electrodes are fixed on the inner core and at least two electrodes are fixed on the cylindrical tube.

3. The probe of claim 2, wherein at least three electrodes are fixed on the inner core and at least three electrodes are fixed on the cylindrical tube.

4. The probe of claim 1, wherein there is overlap between the electrodes on the inner core and electrodes on the cylindrical tube without rotation.

5. The probe of claim 1, further comprising one or more stop bumps located on the outside of the inner core, the inside or the cylindrical tube or both, wherein the stop bump is configured to mechanically stop the one or more electrodes from touching each other.

6. The probe of claim 1, wherein at least one electrode of the plurality of electrodes are asymmetrically shaped.

7. The probe of claim 1, wherein the plurality of electrodes are asymmetrically spaced around the probe or wherein the plurality of electrodes are shaped to provide a sinusoidal type of capacitance readout.

8. The probe of claim 1, wherein the probe is configured or adapted to contain a buffer solution between the tubes.

9. The probe of claim 1, further comprising a hydrophilic coating on at least one of the inner surface of the cylindrical tube or the outer surface of the inner core.

10. The probe of claim 1, further comprising a hydrophobic coating on at least one of the inner surface of the cylindrical tube or the outer surface of the inner core.

11. The probe of claim 1, wherein the cylindrical tube further comprises an imaging window and the plurality of electrodes are located close to or on the imaging window.

12. The probe of claim 11, wherein the outer diameter of the probe is less than 10 mm.

13. The probe of claim 12, wherein at least part of each of the plurality of electrodes are located within 2 cm of the distal end of the probe.

14. The probe of claim 1, further comprising an electronic element connected to the plurality of electrodes, wherein the electronic element is configured to condition the electrodes.

15. The probe of claim 1, wherein the plurality of electrodes are electrically connected with one or more wires.

16. The probe of claim 1, wherein signal from the electrodes can be radiated out and for reception by an antenna.

17. The probe of claim 1, wherein the probe is configured such that the capacitance is between 0.01 pF to 100 nF.

18. A system comprising:
    the probe of claim 1, wherein the inner core comprises a probe adapted for optical coherence tomography or a probe adapted for spectrally encoded endoscopy,
    an electronic detector configured to detect capacitance,
    an optical detector configured to detect light, and
    an analyzer.

19. The system of claim 18, wherein the electronic detector is a capacitance meter based on a PIC microcontroller.

\* \* \* \* \*